United States Patent [19]
Hough

[11] Patent Number: 5,837,716
[45] Date of Patent: Nov. 17, 1998

[54] ANALGESIC HETEROCYCLIC COMPOUNDS

[75] Inventor: Lindsay B. Hough, Slingerlands, N.Y.

[73] Assignee: Albany Medical College, Albany, N.Y.

[21] Appl. No.: 748,467

[22] Filed: Nov. 8, 1996

Related U.S. Application Data

[60] Provisional application No. 60/006,624 Nov. 13, 1995.
[51] Int. Cl.[6] .................. A61K 31/445; A61K 31/415
[52] U.S. Cl. ..................... 514/326; 514/316; 514/317; 514/400
[58] Field of Search ................. 514/400, 316, 514/317, 326

[56] References Cited

U.S. PATENT DOCUMENTS

| | | |
|---|---|---|
| 3,975,530 | 8/1976 | Durant et al. . |
| 4,128,658 | 12/1978 | Price et al. . |
| 4,165,377 | 8/1979 | Jones et al. . |
| 4,172,139 | 10/1979 | Eakins et al. . |
| 4,228,176 | 10/1980 | Eakins et al. . |
| 4,681,883 | 7/1987 | Brown et al. . |
| 4,705,683 | 11/1987 | Dettmar . |
| 4,871,759 | 10/1989 | Mercer . |
| 5,021,431 | 6/1991 | Buschauer et al. . |
| 5,070,101 | 12/1991 | Kaminski . |
| 5,221,688 | 6/1993 | Clitherow et al. . |
| 5,229,137 | 7/1993 | Wolfe . |
| 5,352,688 | 10/1994 | Kaminski . |
| 5,403,830 | 4/1995 | Place . |
| 5,407,688 | 4/1995 | Place . |

OTHER PUBLICATIONS

Black et al., "Definition and Antagonism of Histamine $H_2$–Receptors," *Nature*, 236:385–390 (1972).
Brimblecombe et al., "Histamine $H_2$–Receptor Antagonists," in Goldberg, ed., *Pharmacological and Biochemical Properties of Drug Substances*, Washington, D.C.: American Pharmaceutical Association Academy of Pharmaceutical Sciences, pp. 329–352 (1977).
Netti et al., "Antinociceptive Effect of Centrally Administered Cimetidine and Dimaprit in the Rat," *Pharmacology*, 28:262–267 (1984).
Scarpignato et al., "Cimetidine Inhibition of Dimaprit–Induced Writhing in the Rat," *Pharmacology*, 32:237–240 (1986).
Hough et al., "Cimetidine Penetrates Brain and Inhibits Non–Opiate Footshock–Induced Analgesia," *Pharmacology Biochemistry & Behavior*, 24:1257–1261 (1986).
Netti et al., "Central Effects of Histamine $H_2$–Receptor Agonists and Antagonists on Nociception in the Rat," *Agents and Actions*, 23:247–249 (1988).
Leza et al., "$H_1$–and $H_2$–Histamine Receptor Blockers and Opiate Analgesia in Mice," *Meth Find Exp Clin Pharmacol*, 12:671–678 (1990).
Oluyomi et al., "Involvement of Histamine in Naloxone–Resistant and Naloxone–Sensitive Models of Swim–Stress–Induced Antinociception in the Mouse," *Neuropharmacology*, 30:1021–1027 (1991).
Lamberti et al., "Investigation Into the Role of Histamine Receptors in Rodent Antinociception," *Pharmacology Biochemistry and Behavior*, 53(3):567–574 (1996).
Vyas et al, Chemical Abstracts, vol. 92, abstract No. 104279, 1979.

*Primary Examiner*—William R. A. Jarvis
*Attorney, Agent, or Firm*—Jaeckle Fleischmann & Mugel, LLP; Susan J. Braman, Esq.

[57] ABSTRACT

The present invention discloses that compounds having the formula:

$$R^1 \underset{Z}{\overset{A^1 \quad A^2}{\diagup\diagdown}} D-\underset{X}{\overset{\|}{C}}-NH-R^2$$

wherein

Z represents the atoms necessary to complete a five-membered or six-membered heterocyclic ring;

D is a 1-piperid-4-yl moiety, a —Q—NH— moiety, or a —Q—S— moiety;

Q is a bridging group;

$R^1$ is H, $R^3$ or $R^4$;

$R^2$ is $R^3$;

each of $A^1$ and $A^2$ is H or $A^1$ and $A^2$ taken together form a second bond between the carbon atoms bearing $A^1$ and $A^2$;

X is S, N—CN, $CHNO_2$, O, or NH, provided that when D is a —Q—S— moiety, X is NH;

$R^3$ is selected from the group consisting of substituted or unsubstituted alkyls; substituted or unsubstituted 4-8-membered homocyclic rings; substituted or unsubstituted 4-8-membered heterocyclic rings; substituted or unsubstituted fused multicyclic rings;

$R^4$ is a moiety having the formula:

—W—T

—W— is —O—, —S—, —S—S—, —C(O)—O—, —C(O)—S—, —C(O)—N($R^5$)—, —N($R^5$)—, or CH=N—;

T is selected from the group consisting of substituted or unsubstituted alkyls, substituted or unsubstituted 4-8-membered homocyclic rings, substituted or unsubstituted 4-8-membered heterocyclic rings, substituted or unsubstituted fused multicyclic rings, and proteinaceous transport vectors;

$R^5$ is H, substituted alkyl, or an unsubstituted alkyl and pharmaceutically acceptable salts thereof have analgesic activity. Methods for using these compounds in reducing pain and formulations containing and brain-penetrating derivatives of these compounds are also described.

56 Claims, 4 Drawing Sheets

ANALGESIC HETEROCYCLIC COMPOUNDS

This invention was made with the support of the National Institute on Drug Abuse (Grant No. R01-DA03816). The Federal Government may retain certain rights in the invention.

This application claims the benefit of U.S. Provisional patent application Ser. No. 60/006,624, filed Nov. 13, 1995.

FIELD OF THE INVENTION

The present invention relates to compounds, formulations, and methods for treating pain.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Many, if not most, ailments of the body cause pain. In one sense, pain is a protective mechanism for the body. It occurs whenever any tissues are being damaged, and it causes the individual to react to remove the pain stimulus. Even such simple activities as sitting for prolonged periods on the ischia can cause tissue destruction because of lack of blood flow to the skin where the skin is compressed by the weight of the body. When the skin becomes painful as the result of the ischemia, the person shifts his weight unconsciously. A person who has lost his or her pain sense, such as after spinal cord injury, fails to feel the pain and, therefore, fails to shift his weight. This eventually results in ulceration at the areas of pressure.

Pain, on the other hand, can be an intrusive and destructive response to stimulus. In addition to the discomfort encountered by the individual, pain also results in a lack of concentration, lack of motivation, and reduced ability to function normally. Moreover, continuous sympathetic stimulation, caused by exposure of the individual to pain, has been implicated in the development of mild to moderate hypertension and its destructive secondary effects. In the case of pain stimulation over prolonged periods of time, it is believed that structural changes occur gradually in the kidneys so that permanent pathological hypertension will persist even after removal of the pain stimulus.

Because of the negative effects of pain, much effort has been devoted to alleviating the pain sensation. Previous work has established that the neuromodulator histamine ("HA") is a mediator of analgesia in the central nervous system and induces analgesia after intraventricular administration in rats (Glick and Crane, 1978; Bhattacharya and Parmar, 1985; Parolaro et al., 1989; Sibilia et al., 1992; Braga et al., 1992; Malmberg-Aiello et al., 1994; Netti et al., 1994) and in mice (Onodera and Ogura, 1983; Chung et al., 1984; Malmberg-Aiello et al., 1994). Both $H_1$ and $H_2$ receptors have been implicated in HA antinociception (Glick and Crane, 1978; Bhattacharya and Parmar, 1985; Parolaro et al., 1989; Netti et al., 1988). Antinociception is a reduction in responses to painful stimuli.

It has been recently noted that cimetidine, a known $H_2$ antagonist, also induces analgesia and elicits antinociception after intraventricular (Netti et al., 1984, 1988), intraperitoneal (Oluyomi and Hart, 1991), or subcutaneous (Leza et al., 1990) administration. Other $H_2$ blockers, however, such as tiotidine have been shown to block HA analgesia. Cimetidine also enhances footshock-induced analgesia (Gogas et al., 1986) as well as swim-induced analgesia (Robertson et al., 1988), effects not shared by other $H_2$ antagonists (Gogas and Hough, 1989). In addition, Netti et al, 1984, notes that the analgesic effect of intraventricularly-administered cimetidine is not reversed by the $H_2$ agonist dimaprit. These and other findings suggest that cimetidine analgesia is not mediated by blocking $H_2$ receptors (Netti et al., 1984).

Furthermore, Netti et al., 1984, shows that potency of cimetidine is very low, limiting its practical use as an analgesic.

In view of the importance of attenuating pain perception, the need remains for methods of treating pain. The present invention is directed to overcoming this deficiency in the art.

SUMMARY OF THE INVENTION

The present invention relates to a method for inhibiting pain in a subject. The method includes providing a compound having the formula:

wherein

Z represents the atoms necessary to complete a five-membered or six-membered heterocyclic ring;

D is a 1-piperid-4-yl moiety, a —Q—NH— moiety, or a —Q—S— moiety;

Q is a bridging group;

$R^1$ is H, $R^3$, or $R^4$;

$R^2$ is $R^3$;

each of $A^1$ and $A^2$ is H, or $A^1$ and $A^2$ taken together form a second bond between the carbon atoms bearing $A^1$ and $A^2$;

X is S, N—CN, $CHNO_2$, O, or NH, provided that when D is a —Q—S— moiety, X is NH;

$R^3$ is selected from the group consisting of substituted or unsubstituted alkyls; substituted or unsubstituted 4-8-membered homocyclic rings; substituted or unsubstituted 4-8-membered heterocyclic rings; and substituted or unsubstituted fused multicyclic rings;

$R^4$ is a moiety having the formula:

—W—T

W is —O—, —S—, —S—S—, —C(O)—O—, —C(O)—S—, —C(O)—N($R^5$)—, —N($R^5$)—, or —CH=N—;

T is selected from the group consisting of substituted or unsubstituted alkyls, substituted or unsubstituted 4-8-membered homocyclic rings, substituted or unsubstituted 4-8-membered heterocyclic rings, substituted or unsubstituted fused multicyclic rings, and proteinaceous transport vectors; and $R^5$ is H, substituted alkyl, or an unsubstituted alkyl, provided that when $A^1$ and $A^2$ taken together form a second bond between the carbon atoms bearing $A^1$ and $A^2$, X is N—CN, and Z is —NH—CH=N—, Q is not —$CH_2SCH_2CH_2$— or a pharmaceutically acceptable salt thereof. The method further includes administering to a subject an amount of the compound effective to inhibit pain.

The present invention also relates to method for inhibiting pain in a subject which includes providing a compound having the above formula, altering the compound to make the compound brain-penetrating, and administering to the subject an amount of the altered compound effective to inhibit pain.

In another aspect, the present invention also relates to a compound having the above formula wherein at least one of $R^1$ and $R^2$ is lipophilic.

In still another aspect, the present invention provides a composition containing the above compound and a material which enhances brain penetration of the above compound.

The methods, compounds, and compositions of the present invention are useful in inhibiting pain. The compounds of the present invention have higher pain—relieving potency than cimetidine and, in many cases, lack significant $H_1$ and $H_2$ properties so as not to interfere with the normal function of these receptors. Moreover, at high doses, the compounds do not exert an opposing pro-nociceptive response which is commonly observed when histamine ("HA") is employed to relieve pain.

BRIEF DESCRIPTION OF THE DRAWINGS

FIG. 2 depicts the antinociceptive effects of SKF92374 administered intracerebrally. Rats were tested for baseline hot plate responses, received a single intracerebral microinjection (0.5 µl) into the ventral, rostral periaqueductal grey, and were re-tested 10 min later. Animals received either SKF92374 (triangles) or saline control (SAL). Hot plate responses (mean % MPE+S.E.M., n=4–11) are plotted vs dose (log scale). Baseline scores were not different between the groups. ANOVA showed significant effects of the drug. Asterisks and double asterisks indicate data having P less than 0.05 and 0.01, respectively vs SAL.

FIGS. 3A and 3B are dose-response curves for SKF92374, cimetidine, and HA on the hot plate (A) and the tail flick (B) nociceptive tests. Animals were tested for baseline nociception, received an intraventricular injection (5 µl), and were re-tested 10 minutes after injection. The doses of drugs (µg, abscissa, log scale) are plotted against the antinociceptive scores (mean % MPE±S.E.M., ordinate, 10 min after injection, n=4–11) for HA (inverted solid triangles), cimetidine (open squares), and SKF92374 (solid circles). As described in Example 3, data were fitted to estimate $ED_{50}$ (11g shown) and slope function of each curve. S.E.M. values for the highest HA dose (100 µg) were omitted for clarity. These values were 17.9 and 21.9 for A and B, respectively.

DETAILED DESCRIPTION

The present invention relates to a method for inhibiting pain. One aspect of the present invention relates to a method which includes providing a compound having the formula:

Each of $A^1$ and $A^2$ can by hydrogen, or $A^1$ and $A^2$ taken together can form a second bond between the carbon atoms bearing $A^1$ and $A^2$.

Z represents the atoms necessary to complete a five-membered or six-membered heterocyclic ring. Typically these atoms are selected from carbon, oxygen, sulfur, selenium, or nitrogen, with at least one of the atoms being non-carbon. The ring can be aromatic or non-aromatic and may, optionally, include one or more double bonds. For example Z can be —O—CH₂—CH₂—, —CH₂—O—CH₂—, —CH₂—CH₂—O—, —S—CH₂—CH₂—, —CH₂—S—CH₂—, —CH₂—CH₂—S—, —Se—CH₂—CH₂—, —CH₂—Se—CH₂—, —CH₂—CH₂—Se—, —NH—CH₂—CH₂—, —CH₂—NH—CH₂—, —CH₂—CH₂—NH—, —O—CH₂—O—, —O—CH₂—S—, —S—CH₂—O—, —O—S—CH₂—, —CH₂—S—O—, —S—O—CH₂—, —CH₂—O—S—, —O—CH₂—Se—, —Se—CH₂—O—, —O—Se—CH₂—, —CH₂—Se—O—, —Se—O—CH₂—, —CH₂—O—Se—, —O—CH₂—NH—, —NH—CH₂—O—, —CH₂—O—NH—, —NH—O—CH₂—, —CH₂—NH—O—, —O—NH—CH₂—, —NH—CH₂—NH—, —NH—NH—CH₂—, —CH₂—NH—NH—, —S—CH₂—S—, —S—S—CH₂, —CH₂—S—S—, —S—CH₂—Se—, —Se—CH₂—S—, —S—Se—CH₂—, —CH₂—Se—S—, —Se—S—CH₂—, —CH₂—S—Se—, —NH—CH₂—S—, —S—CH₂—NH—, —S—NH—CH₂—, —CH₂—NH—S—, —NH—S—CH₂—, —CH₂—S—NH—, —NH—CH₂—Se—, —Se—CH₂—NH—, —CH₂—NH—Se—, —Se—NH—CH₂—, —NH—Se—CH₂—, —CH₂—Se—NH—, —Se—CH₂—Se—, —Se—Se—CH₂—, —CH₂—Se—Se—, —S—S—S—, —Se—Se—Se—, —NH—NH—NH—, —O—S—O—, —O—S—S—, —S—O—S—, —S—S—O—, —O—Se—O—, —O—Se—Se—, —Se—O—Se—, —Se—Se—O—, —O—NH—O—, —NH—NH—, —NH—O—NH—, —NH—NH—O—, —S—S—Se—, —S—Se—S—, —Se—S—S—, —Se—S—Se—, —Se—Se—S—, —S—Se—Se—, —S—S—NH—, —S—NH—S—, —NH—S—S—, —NH—NH—S—, —NH—S—NH—, —S—NH—NH—, —Se—Se—NH—, —Se—NH—Se—, —NH—Se—Se—, —NH—NH—Se—, —Se—NH—NH—, —NH—Se—NH—, —NH—O—S—, —NH—O—Se—, —O—NH—S—, —O—NH—Se—, —S-0—NH—, —Se—O—NH—, —O—S—Se—, —O—Se—S—, —S—O—Se—, —S—Se—O—, —Se—O—S—, —Se—S—O—, —NH—S—Se—, —NH—Se—S—, —S—NH—Se—, —S—Se—NH—, —Se—NH—S—, —Se—S—NH—, —O—CH=CH—, —CH=CH—O—, —S—CH=CH—, —CH—CH—S—, —Se—CH=CH—, —CH=CH—Se—, —NH—CH=CH—, —N=CH—CH₂—, —CH=N—CH₂—, —CH₂—N=CH₂—, —CH₂—CH=N—, —CH=CH—NH—, —O—CH=N—, —N=CH—O—, —CH=N—O—, —O—N=CH₂—, —N=CH—S—, —S—CH=N—, —S—N=CH—, —CH=N—S—, —N=CH—NH—, —NH—CH=N—, —N=N—CH₂—, —NH—N=CH—, —CH=N—NH—, —CH₂—N=N—, —N=CH—Se—, —Se—CH=N—, —CH=N—Se—, —Se—N=CH—, —NH—N=N—, —N=N—NH—, —O—N=N—, —N=N—O—, —N=N—S—, —S—N=N—, —N=N—Se—, —Se—N=N—, —CH₂—CH₂—CH₂—O—, —CH₂—CH₂—O—CH₂—, —CH₂—O—CH₂—CH₂—, —O—CH₂—CH₂—CH₂—, —CH₂—CH₂—CH₂—S—, —CH₂—CH₂—S—CH₂—, —CH₂—S—CH₂—CH₂—, —S—CH₂—CH₂—CH₂—, —CH₂—CH₂—CH₂—Se—, —CH₂—CH₂—Se—CH₂—, —CH₂—Se—CH₂—CH₂—, —Se—CH₂—CH₂—CH₂—, —CH₂—CH₂—CH—NH—, —CH₂—CH₂—NH—CH₂—, —CH₂—NH—CH₂—CH₂—, —NH—CH₂—CH₂—CH₂—, —CH₂—O—CH₂—O—, —O—CH₂—CH₂—O—, —O—CH₂—O—CH₂—, —CH₂—CH₂—S—S—, —CH₂—S—CH₂—S—, —CH₂—S—S—CH₂—, —S—CH₂—CH₂—S—, —S—CH₂—S—CH₂—, —S—S—CH₂—CH₂—, —CH₂—CH₂—Se—Se—, —CH₂—Se—CH₂—Se—, —CH₂—Se—Se—CH₂—, —Se—CH₂—CH₂—Se—, —Se—CH₂—Se—CH₂—, —Se—Se—CH₂—CH₂—, —CH₂—CH₂—NH—NH—, —CH₂—NH—CH₂—NH—, —CH₂—NH—NH—CH₂—, —NH—CH₂—CH₂—NH—, —NH—CH₂—NH—CH₂—, —NH—NH—CH₂—CH₂—, —CH₂—CH₂—O—S—, —CH₂—CH₂—S—O—, —CH₂—O—CH₂—S—, —CH₂—S—CH₂—O—, —CH₂—O—S—CH₂—, —CH₂—S—O—CH₂—, —O—CH₂—CH₂—S—, —S—CH₂—CH₂—O—, —O—CH₂—S—CH₂—, —S—CH₂—O—CH₂—, —O—S—CH₂—CH₂—, —S—O—CH₂—CH₂—, —CH₂—CH₂—O—Se—, —CH₂—CH₂—Se—O—, —CH₂—O—CH₂—Se—, —CH—Se—CH₂—O—, —CH₂—O—Se—CH₂—, —CH₂—Se—O—CH₂—, —O—CH₂—CH₂—Se—, —Se—CH₂—CH₂—O—, —O—CH₂—Se—CH₂—, —Se—CH₂—O—CH₂—, —O—Se—CH₂—CH₂—, —Se—O—CH₂—CH₂—, —CH₂—CH₂—O—NH—, —CH₂—CH₂—NH—O—, —CH₂—O—CH₂—NH—, —CH₂—NH—CH₂—O—, —CH₂—O—NH—CH₂—, —CH₂—NH—O—CH₂—, —O—CH₂—CH₂—NH—, —NH—CH₂—CH₂—O—, —O—CH₂—NH—CH₂—, —NH—CH₂—O—CH₂—, —O—NH—CH₂—CH₂—, —NH—O—CH₂—CH₂—, —CH₂—CH₂—S—Se—, —CH₂—CH₂—Se—S—, —CH₂—S—CH₂—Se—, —CH₂—Se—CH₂—S—, —CH₂—S—Se—CH₂—, —CH₂—Se—S—CH₂—, —S—CH₂—CH₂—Se—, —Se—CH₂—CH₂—S—, —S—CH₂—Se—CH₂—, —Se—CH₂—CH₂—S—, —S—Se—CH₂—CH₂—, —Se—S—CH₂—CH₂—, —CH₂—CH₂—S—NH—, —CH₂—CH₂—NH—S—, —CH₂—S—CH₂—NH—, —CH₂—NH—CH₂—S—, —CH₂—S—NH—CH₂—, —CH₂—NH—S—CH₂—, —S—CH₂—CH₂—NH—, —NH—CH₂—CH₂—S—, —S—CH₂—NH—CH₂—, —NH—CH₂—S—CH₂—, —S—NH—CH₂—CH₂—, —NH—S—CH₂—CH₂—, —CH₂—CH₂—NH—Se—, —CH₂—CH₂—Se—NH—, —CH—NH—CH₂—Se—, —CH₂—Se—CH₂—NH—, —CH₂NH—Se—CH₂—, —CH₂—Se—NH—CH₂—, —NH—CH₂—CH₂—Se—, —Se—CH₂—CH₂—NH—, —NH—CH₂—Se—CH₂—, —Se—CH₂—NH—CH₂—, —NH—Se—CH₂—CH₂—, —Se—NH—CH₂—CH₂—, —CH=CH—CH₂—O—, —CH₂—CH=CH—O—, —CH=CH—O—CH₂—, —CH₂—O—CH=CH—, —O—CH=CH—CH₂—, —O—CH₂—CH=CH—, —CH=CH—CH₂—S—, —CH₂—CH=CH—S—, —CH=CH—S—CH₂—, —CH₂—S—CH=CH—, —S—CH=CH—CH₂—, —S—CH₂—CH=CH—, —CH=CH—CH₂—Se—, —CH₂—CH=CH—Se—, —CH=CH—Se—CH₂—, —CH₂—Se—CH=CH—, —Se—CH=CH—CH₂—, —Se—CH₂—CH=CH—, —CH=CH—CH₂—NH—, —CH₂—CH=CH—NH—, —CH₂—CH₂—CH=N—, —CH=CH—CH=N—, —CH=CH—NH—CH₂—, —CH₂—CH=N—CH₂—, —CH₂—CH₂—N=CH—, —CH=CH—N=CH—, —CH=N—CH₂—CH₂—, —CH₂—N=CH—CH₂—, —CH—NH—CH=CH—, —CH=N—CH=CH—, —N=CH—CH₂—CH₂—, —NH—CH=CH—CH₂—, —NH—CH₂—CH=CH—, —N=CH—CH=CH—, —CH=CH—S—S—, —S—CH=CH—S—, —S—S—CH=CH—, —CH=CH—Se—Se—, —Se—CH=CH—Se—, —Se—Se—CH=CH—, —CH=CH—NH—NH—, —CH₂—CH=N—NH—, —CH₂—CH₂—N=N—, —CH=CH—N=N—, —CH=N—CH₂—NH—, —CH₂—N=CH—NH—, —CH₂—NH—CH=N—, —CH=N—CH=N—, —CH=N—NH—CH₂—, —CH₂—N=N—CH₂—, —CH₂—NH—N=CH—, —CH=N—N=CH—, —N=CH—CH₂—NH—, —NH—CH=CH—NH—, —NH—CH₂—CH=N—, —N=CH—CH=N—, —N—CH₂—N=CH—, —CH₂—N—CH=N—, —N=CH—N=CH—, —N=N—CH₂—CH₂—, —NH—N=CH—CH₂—, —NH—NH—CH=CH—, —N=N—CH=CH—, —CH=CH—O—S—, —CH=CH—S—O—, —O—CH=CH—S—, —S—CH=CH—O—, —O—S—CH=CH—, —S—O—CH=CH—, —CH—CH—O—Se—, —CH=CH—Se—O—, —O—CH=CH—Se—, —Se—CH=CH—O—, —O—Se—CH=CH—, —Se—O—CH=CH—, —CH=CH—S—Se—, —CH=CH—Se—S—, —S—CH=CH—Se—, —Se—CH=CH—S—, —S—Se—CH=CH—, —Se—S—CH=CH—, —CH=CH—O—NH—, —CH=CH—NH—O—, —CH₂—CH=N—O—, —CH₂—O—CH=N—, —CH=N—CH₂—O—, —CH₂—N=CH—O—, —CH₂—O—N=CH—, —CH=N—O—CH₂—, —O—CH=CH—NH—, —O—CH₂—CH=N—, —N=CH—CH₂—NO—, —NH—CH=CH—O—, —O—CH=N—CH₂—, —O—CH₂—N=CH—, —N=CH—O—CH₂—, —O—N=CH—CH₂—, —O—NH—CH=CH—, —NH—O—CH=CH—, —CH=CH—S—NH—, —CH=CH—NH—S—, —CH₂—CH=N—S—, —CH₂—S—CH=N—, —CH=N—CH₂—S—, —CH₂—N=CH—S—, —CH₂—S—N=CH—, —CH=N—S—CH₂—, —S—CH=CH—NH—, —S—CH₂—CH=N—, —N=CH—CH₂—S—, —NH—CH=CH—S, —S—CH=N—CH₂—, —S—CH₂—N=CH—, —N=CH—S—CH₂—, —S—N=CH—CH₂—, —S—NH—CH=CH—, —NH—S—CH=CH—, —CH=CH—NH—Se—, —CH₂—CH=N—Se—, —CH=CH—Se—NH—, —CH=N—CH₂—Se—, —CH₂—N=CH—Se—, —CH₂—Se—CH=N—, —CH=N—Se—CH₂—, —CH₂—Se—N=CH—, —N=CH—CH₂—Se—, —NH—CH=CH—Se—, —Se—CH=CH—NH—, —Se—CH₂—CH=N—, —N=CH—Se—CH₂—, —Se—CH=N—CH₂—, —Se—CH₂—N=CH—, —NH—Se—CH=CH—, and —Se—NH—CH=CH—. Z is preferably —NH—CH=N—, —S—CR⁶=N—, or —CH—CR⁶=O—.

As indicated above, the heterocyclic ring can be substituted or unsubstituted. Substitution in the context of the ring means that one or more of the hydrogens on the carbons or nitrogens or the ring are replaced with one or more substituents, such as a halogen, hydroxy, thiol, substituted or unsubstituted alkyl, substituted or unsubstituted aryl, substituted or unsubstituted alkoxy or aryloxy, substituted or unsubstituted alkylthio or arylthio, substituted or unsubstituted amine, substituted or unsubstituted imine, and the like. The substituents on the heterocyclic ring can combine to form a heterocyclic or homocyclic ring fused to the 5- or 6-membered heterocyclic ring. Where the atoms making up Z are substituted with other than hydrogen, preferred substituents are substituted imines and the substituted or unsubstituted lower (C1–C6) alkyls, preferably amine-substituted lower alkyls, such as dimethylaminomethyl. In particular, when Z is —NH—CH=N—, Z is preferably unsubstituted; when Z is —S—CR$^6$=N—, R$^6$ is preferably —N=C(NH$_2$)$_2$; and when Z is —CH=CR$^6$—O—, R$^6$ is preferably —CH$_2$—N(CH$_3$)$_2$.

The atoms which constitute Z, together with the two carbon atoms to which Z is bonded, make up the heterocyclic nucleus of the compound. Suitable heterocyclic nuclei contemplated by the present invention include, for example, thiophene, furan, 2H-pyran, 4H-pyran, pyrrole, 2H-pyrrole, pyrazine, pyridine, pyrazole, imidazole, pyrimidine, pyridazine, isothiazole, isoxazole, pyrrolidine, pyroline, imidazolidine, imidazoline, pyrazolidine, pyrazoline, piperidine, piperazine, indoline, morpholine, 1,3-dioxacyclohexane, 1,4-dioxacyclohexane, dithiazine, thiadiazine, oxathiolane, oxazolidine, thiazolidine, benzothiazole, benzothiazoline, bezoxazole, benzoxazoline, bezimidazole, benzimidazoline, and the like.

R$^2$ is R$^3$. R$^1$ on the other hand can be H, R$^3$, or R$^4$.

R$^3$ can be an alkyl. Suitable alkyls include an unsubstituted alkyl, such as, methyl, ethyl, n-propyl, iso-propyl, n-butyl, sec-butyl, tert-butyl, n-pentyl, sec-pentyl, neo-pentyl, hexyl, heptyl, octyl, nonyl, decyl, dodecyl, dodecyl, eicosyl, docosyl, and the like. Alternatively, the alkyl can be substituted with any of a number of known substituents, such as sulfo, carboxy, cyano, halogen (e.g., fluoro, chloro), hydroxy, alkenyl (e.g., allyl, 2-carboxy-allyl), alkoxy (e.g., methoxy, ethoxy), aryloxy (e.g., phenyloxy), carboxylate (e.g., methoxycarbonyl, ethoxycarbonyl), acyloxy (e.g., acetyloxy), acyl (e.g., acetyl, propionyl), and others known to those skilled in the art. In addition, substituted alkyls include arylalkyls, such as 2-phenyleth-1-yl, 2-phenylprop-1-yl, benzyl, and arylalkyls bearing substitutents on the aromatic ring, such as 2-(5-chlorophenyl)prop-1-yl, N-piperidino, N-pyrrolidino, and N-morpholino. The alkyl can also be substituted with substituted or unsubstituted 4-8-membered homocyclic rings, substituted or unsubstituted 4-8-membered heterocyclic rings, and substituted or unsubstituted fused multicyclic rings, examples for each of which are provided below.

Alternatively, R$^3$ can be a 4-8-membered homocyclic ring, such as cyclopentyl, cyclohexyl, cyclohexenyl, and phenyl; a homocyclic ring system, such as naphthyl; a 4-8-membered heterocyclic ring, such as pyrrolyl, imidazolyl, pyrimidinyl, thiazolyl, and furyl; or a heterocyclic ring system, such as benzothienyl, purinyl, isoquinolyl, quinidyl, benzothiazolyl, benzimidazolyl, and bezoxazolyl. R$^3$ can also be a fused multicyclic homocyclic or heterocyclic ring system, such as tricyclo[3.3.1.1$^{3,7}$]decane (adamantane), bicyclo[2.2.1]heptane (norbornane), tricyclo [5.3.2.0] dodecane, quinuclidine, 7-azabicyclo[2.2.1] heptane, and the like. The homocyclic ring or ring system, heterocyclic ring or ring system, and fused multicyclic homocyclic or heterocyclic ring system can, optionally, be substituted.

R$^4$ is a moiety having the formula:

—W—T

W is —O—, —S—, —S—S—, —C(O)—O—, —C(O)—S—, —C(O)—N(R$^5$)—, —N(R$^5$)—, or —CH=N—. T is selected from the group consisting of substituted or unsubstituted alkyls, substituted or unsubstituted 4-8-membered homocyclic rings, substituted or unsubstituted 4-8-membered heterocyclic rings, substituted or unsubstituted fused multicyclic rings, examples for each of which are the same as those provided above with respect to R$^3$. In addition T can be a proteinaceous transport vector, such as monoclonal antibodies to the transferrin receptor, the preparation and use of which to enhance brain penetration has been described in Pardridge, 1992. When T represents a proteinaceous transport vector, it is typically coupled to the heterocyclic nucleus via an ester, a thioether, a Schiff base, or a disulfide moiety.

D is a 1-piperid-4-yl moiety, a —Q—NH— moiety, or a —Q—S— moiety. In the case where D is a —Q—NH— moiety, the compounds of the present invention have the formula:

In the case where D is —Q—S— moiety, the compounds of the present invention have the formula:

In the case where D is a 1-piperid-4-yl moiety, the compounds of the present invention have the formula:

Q is a bridging group. Suitable bridging groups include those having the formula

—(CH$_2$)$_m$—(Y)$_s$—(CH$_2$)$_n$—

Y can be O, S, Se, or NH; m and n, which can be the same or different, are integers from 0 to 5, and s can be 0 or 1. Where s is 0, the bridging group is simply a linear alkylene moiety having a number of carbons equal to the sum of m and n. Where s, m, and n are all zero, Q simply represents a single bond directly between the nitrogen and the carbon to which it is bonded. Particularly useful bridging groups include those where the sum of m, n, and s is three, four, or six, such as, for example, —CH$_2$—CH$_2$—CH$_2$—, —CH$_2$—S—CH$_2$—, —CH$_2$—CH$_2$—CH$_2$—CH$_2$—, —CH$_2$—S—CH$_2$—CH$_2$—, —CH$_2$—CH$_2$—CH$_2$—CH$_2$—CH$_2$—CH$_2$—, and —CH$_2$—S—CH$_2$—CH$_2$—CH$_2$—CH$_2$—.

X can be S, N—CN, CHNO$_2$, O, or NH. In the case where D is a —Q—S— moiety, X is preferably NH.

Where D is a —Q—NH— moiety, the side chain corresponding to —Q—NH—C(=X)—NH— is preferably selected from the group consisting of —CH$_2$—CH$_2$—CH$_2$—NH—C(=S)—NH—, —CH$_2$—CH$_2$—CH$_2$—NH—C(=NCN)—NH—, —CH$_2$—CH$_2$—CH$_2$—CH$_2$—NH—C(=S)—NH—, —CH$_2$—S—CH$_2$—CH$_2$—NH—C(=S)—NH—, —CH$_2$—S—CH$_2$—CH$_2$—NH—C(=NCN)—NH—, —CH$_2$—S—CH$_2$—CH$_2$—NH—C(=CHNO$_2$)—NH—, and —CH$_2$—CH$_2$—CH$_2$—CH$_2$—CH$_2$—CH$_2$—NH—C(=S)—NH—.

Preferred compounds for use in the methods of the present invention include those having the formulae:

illustrative examples of which are burimamide, metiamide, tiotidine, ranitidine, norburimamide, and SKF92374, which, respectively, are represented by the following formulae:

Other illustrative examples of the preferred compounds for use in the methods of the present invention include VUF 4685, VUF 4684, VUF 4686, VUF 4687, VUF 4740, VUF 4741, VUF 5261, and VUF 5262, which, respectively, have the following formulae:

Preferred compounds are those which lack potent $H_3$ receptor blocking activity. As used herein, potent $H_3$ blockers are those having an $H_3$ receptor dissociation constant ("$K_D$") of 10 nM or less. $K_D$ can be evaluated by in vitro tests, such as the intestine $H_3$ assay, which is described in Vollinga et al., 1992.

Some of the aforementioned compounds are commercially available. For example, ranitidine is available from Glaxo (Middlesex, England). Alternatively, the compounds described above can be prepared by well known synthetic procedures and schemes, such as those described in Vollinga et al., 1995.

Briefly, compounds having the formula:

can be conveniently prepared by treating an appropriate heterocyclic amine precursor having the formula:

with a substituted or unsubstituted alkyl or aryl isothiocyanate having the formula $R^2$—NCS. The reaction can be performed in a variety of solvents and under a range of conditions. For example, an appropriate heterocyclic amine precursor, such as an imidazolylalkylamine, can be dissolved in alcohol or water and refluxed, typically for about 5 minutes to about 5 hours, preferably about 0.5 hour, with methyl isothiocyanate to produce the intended thiourea (Durant et al., 1977). Where the heterocyclic amine precursor is a furan having the formula:

this reaction is preferably conducted in acetonitrile for several hours (Price et al., 1978).

Cyanoguanidine derivatives having the formula:

can be prepared from the corresponding thiourea, synthesized as described above by reaction of the thiourea with a heavy metal salt of cyanamide, such as PbNCN, in a suitable solvent, preferably acetonitrile or dimethylformamide (Durant et al., 1977; Durant et al., 1976).

Alternatively, cyanoguanidine derivatives can be prepared directly from the heterocyclic amine precursor having the formula:

by sequentially first reacting the heterocyclic amine precursor with a dialkyl-N-cyanothioiminocarbonate, such as dimethyl-N-cyanothioiminocarbonate ($CH_3$—S—C(=NCN)—S—$CH_3$), in an appropriate solvent, preferably ethanol, and at a temperature from room temperature to the reflux temperature of the solvent. The resulting intermediate is then treated with an alkyl amine having the formula $R^2NH_2$, preferably at room temperature (Durant et al., 1977; Durant et al., 1976; Jones et al., 1979).

Compounds bearing nitroethene substitutents and having the formula:

can be prepared from the heterocyclic amine precursor by reacting the precursor with an appropriate N-substituted-1-alkylthio-2-nitroethanamine, such as N-substituted-1- methylthio-2-nitroethanamine ($CH_3$—S—C(=$CHNO_2$)—NH—$R^2$), where the amine nitrogen is substituted with the desired $R^2$ group. The reaction can be performed in water or other suitable solvents and typically requires mild heating conditions (Price et al., 1978). Suitable N-substituted-I-alkylthio-2-nitroethanamines can be prepared by the methods described in Price et al., 1978.

Compounds of the present invention in which D is a 1-piperid-4-yl moiety can be prepared by the above methods using a heterocyclic amine precursor having the formula:

Depending on the nature of the heterocyclic ring, the nature of the bridging group Q, or both, the heterocyclic amine precursors used in the above reactions can be obtained commercially, or, alternatively, they can be prepared by methods well known in the art, such as those described in Schwartz et al., 1990, and in Arrang et al, 1987. When Q is a thioether, i.e. $(CH_2)_m$—S—$(CH_2)_n$, the heterocyclic amine precursor can be readily synthesized by condensation of an alcohol or halide precursor having the formula:

where G is OH or a halide, such as Cl, Br, or I, with a mercaptoalkylamine having the formula HS—$(CH_2)_n$—$NH_2$.

The aforementioned compounds are useful in treating subjects, such as mammals and including rats and humans, to inhibit, reduce, or prevent the occurrence of pain, by administering the compounds to such subjects in an effective amount. The compounds of the present invention may be administered alone or in combination with suitable pharmaceutical carriers or diluents. The diluent or carrier ingredients should be selected so that they do not diminish the therapeutic effects of the compounds of the present invention.

The compounds herein may be made up in any suitable form appropriate for the desired use; e.g., oral, parenteral, or topical administration. Examples of parenteral administration are intraventricular, intracerebral, intramuscular, intravenous, intraperitoneal, rectal, and subcutaneous administration.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

For oral administration either solid or fluid unit dosage forms can be prepared. For preparing solid compositions, such as tablets, a suitable compound as disclosed above is mixed with conventional ingredients, such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the disclosed compound with an inert pharmaceutical diluent and filling the fixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents, and preservatives to form a syrup. An elixir is prepared by using a hydro-alcoholic (ethanol) vehicle with suitable sweeteners, such as sugar and saccharin, together with an aromatic flavoring agent. Suspensions can be prepared with a syrup vehicle with the aid of a suspending agent, such as acacia, tragacanth, methylcellulose, and the like.

When the compounds are administered orally, suitable daily dosages are from about 3 to about 25 mg of compound per kilogram of the subject's body weight.

For parenteral administration, fluid unit dosage forms are prepared utilizing the aforementioned compounds and a sterile vehicle, water being preferred. The compound, depending on the vehicle and concentration used, can be either suspended or dissolved in the vehicle. In preparing solutions, the compound can be dissolved in water for injection and filter sterilized before filling into a suitable vial or ampule and sealing. Advantageously, adjuvants, such as a local anesthetic, preservative, and buffering agents, can be dissolved in the vehicle. To enhance the stability, the composition can be frozen after filling into the vial, and the water removed under vacuum. The dry lyophilized powder is then sealed in the vial, and an accompanying vial of water for injection is supplied to reconstitute the liquid prior to use. Parenteral suspensions are prepared in substantially the same manner except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound. Parenteral dosages can range from about 1 to about 8 mg of compound per kilogram of the subject's body weight per day.

Because it is believed that the compounds operate on one or more of the several brain stem areas involved in pain control, and in view of the difficulties encountered in penetrating the blood-brain barrier, it is preferred that the compounds be administered intracerebrally or intraventricularly, preferably in the form of a sterile saline solution. Typical intracerebral doses are from about 30 to about 100 μg, and administration is effected by injecting the compound into the periaqueductal grey, the rostral, the ventral medulla, or other areas. Intraventricular administration is generally effected by delivering the dosage into the third or fourth ventricle. Suitable intraventricular doses are from about 5 to about 40 mg, and may be repeated every 2 to 4 hours, as needed.

Alternatively, the compound can be incorporated into a sustained release formulation and surgically implanted using conventional methods into the brain, preferably into the periaqueductal grey area of the brain. Suitable sustained release matricies include those made of ethylene vinyl acetate and other bicompatible polymers. Sustained release formulations are prepared by methods standard in the art, such as those described in Madrid et al., 1991.

Delivery of the compounds to the brain can also be enhanced by co-administering agents known to open the blood-brain barrier. By co-administration is meant administering the agent before, during (together or separately), or after administering the compound but within a time such that both the compound and the agent are present in the subject at the same time. Suitable agents known to open the blood brain barrier include hyperosmotic sugar solutions, such as solutions of mannitol or L-arabinose, as described in Madrid et al., 1991. Preferably, the hyperosmotic sugar solution is administered by injection into the caotid artery, about 5 to 15 minutes before administration of the compound as described in Neuwelt et al., 1984.

The present invention also relates to compounds which are derivatized so as to enhance their brain-penetration. Derivatization, as used herein, refers to a covalently bonded lipophilic moiety. Derivatization can be achieved on any atom of the heterocyclic nucleus which has an available hydogen (such as carbon or $sp^3$ hybridized nitrogens. Alternatively or additionally, $R^1$, $R^2$, or both can be selected so as to provide the desired lipophilic property. The mode of attachment of the lipophilic moiety is not critical, and can be effected by a carbon-carbon, carbon-oxygen, carbon-nitrogen, or carbon-sulfur bond. To maximize the lipophilicity of the resulting compound, however, it is preferred that attachment be effected so as to minimize polarity. Consequently, it is preferred that the lipophilic moiety be attached via a carbon-carbon bond. The lipophilic moiety can be a hydrocarbon, such as an alkyl having from 5 to 20 carbons. These alkyls can be unsubstituted, such as hexyl or dodecyl, or substituted, such as with an aryl moiety, as in the case where the substituted alkyl is a benzyl or a phenylethyl group. Alternatively, the lipophilic moiety can be substituted or unsubstituted homocyclic rings, such as phenyl groups or a tolyl groups, homocyclic ring systems, heterocyclic rings, heterocyclic ring systems, or multicyclic lipophilic "cage" moieties, such as adamantane. In particular, the use of the multicyclic "cage" compounds are particularly advantageous (Tsuzuki, 1991).

The present invention further relates to compositions comprising the aforementioned compound and a material which enhances the delivery of the active compounds to the brain (i.e. to penetration the blood-brain barrier). Materials for use in such compositions are described in Pardridge, 1992, and in Allen and Everest, 1983. Suitable materials include those which entrap the compounds in phospholipid vessicles, such as multilamellar vessicles or reverse-phase evaporated vessicles (Allen and Everest, 1983, and Fresta et al., 1994).

Suitable phospholipids include negatively-charged phospholipids, positively-charged phospholipids, and zwitterionic phospholipids. Suitable phospholipids include phosphatidyl inositol, phosphatidyl serine, phosphatidyl glycerol, phosphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, brain phosphatidyl serine, phosphatidyl choline, phosphatidyl ethanolamine, sphingomyeline, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-2-stearoyl phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof.

Although, phospholipid content of the liposomes can vary considerably, they advantageously can include forms of phosphatidyl choline (lecithin, e.g. 1,2-dipalmitoyl-sn-glycero-3-phosphocholine), phosphotidyl ethanolamine (e.g. 1,2-dipalmitoyl-sn-glycero-3-phosphoetanolamine), phosphotidyl serine (e.g. 1,2-sipalmitoyl-DL-α-phosphatidyl-L-serine), and cholesterol, in various combinations.

Liposomes are completely closed bilayer membranes containing an encapsulated aqueous phase. Liposomes may be any of a variety of multilamellar vesicles ("MLV") (onion-like structures characterized by concentric membrane bilayers each separated by an aqueous layer) or unilamellar vesicles (possessing a single membrane bilayer).

The following parameters of liposome preparations are functions of vesicle size and lipid concentration as follows: (1) Captured volume, defined as the volume enclosed by a given amount of lipid, is expressed as units of liters entrapped per mole of total lipid (liters/mole) and (2) Encapsulation efficiency, defined as the fraction of the aqueous compartment sequestered by the bilayers, is expressed as a percentage. The captured volume depends upon the radius of the liposomes and the number of internal membrane bilayers which in turn is affected by the lipid composition of the vesicles and the ionic composition of the medium. The encapsulation efficiency is directly proportional to the lipid concentration; when more lipid is present, more solute can be sequestered within liposomes. (See Deamer and Uster, 1983.)

Methods for preparing compounds containing liposome suspensions generally follow conventional liposome preparation methods, such as those reviewed by Szoka et al., 1980.

In one method, vesicle-forming lipids are taken up in a suitable organic solvent or solvent system, and dried (or lyophilized) in vacuo or under an inert gas to a lipid film. The aforementioned compounds are preferably included in the lipids forming the film. The concentration of compound in the lipid solution may be included in molar excess of the final maximum concentration of compound in the liposomes, to yield maximum drug entrapment in the liposomes.

The aqueous medium used in hydrating the dried lipid or lipid/compound is a physiologically compatible medium, preferably a pyrogen-free physiological saline or 5% dextrose in water, as used for parenteral fluid replacement. The lipids are allowed to hydrate under rapid conditions (using agitation) or slow conditions (without agitation). The lipids hydrate to form a suspension of multilamellar vesicles whose size range is typically from about 0.5 microns to about 10 microns or greater. In general, the size distribution of MLVs in the above procedure can be shifted toward smaller sizes by hydrating the lipid film more rapidly while shaking. The structure of the resulting membrane bilayer is such that the hydrophobic (non-polar) "tails" of the lipid orient toward the center of the bilayer, while the hydrophilic (i.e. polar) "heads" orient towards the aqueous phase.

In another method, dried vesicle-forming lipids and an above-described pain-relieving compound, mixed in the appropriate amounts, are dissolved, with warming if necessary, in a water-miscible organic solvent or mixture of solvents. Examples of such solvents are ethanol, or ethanol and dimethylsulfoxide (DMSO) in varying ratios. The compound/lipid/solvent mixture then is added to a sufficient volume of aqueous phase to cause spontaneous formation of liposomes. The aqueous phase may be warmed if necessary to maintain all lipids in the melted state. The aqueous phase may be stirred rapidly or agitated gently. The compound/lipid/solvent mixture may be injected rapidly through a small orifice, or poured in directly. After incubation of several minutes to several hours, the organic solvents are removed, for example, by reduced pressure or dialysis, leaving a liposome suspension suitable for human administration.

In another method, the compound and dried vesicle-forming lipids, mixed in the appropriate amounts, are dissolved, with warming if necessary, in a suitable organic solvent with a vapor pressure and freezing point sufficiently high to allow removal by freeze-drying (lyophilization). Examples of such solvents are tert-butanol and benzene. The compound/lipid/solvent mixture then is frozen and placed under high vacuum. Examples of methods for freezing include "shell-freezing", in which the container containing the compound/lipid/solvent mixture is swirled or spun to maximize contact of the liquid with the walls of the vessel, and the container is placed in a cooled substance such as liquid nitrogen or carbon dioxide ice mixed with a solvent such as an alcohol or acetone. The mixture thus is frozen rapidly without segregation of the constituents of the compound/lipid/solvent mixture. A fluffy, dry powder results from removal of the solvent by lyophilization. This compound/lipid powder may be stored for extended periods under conditions that reduce chemical degradation of the constituents or the absorption of moisture. Examples of such conditions include sealed under an atmosphere of dry, inert gas (such as argon or nitrogen), and storage in the cold. When it is desired to administer the material, reconstitution is performed by adding a physiologically compatible aqueous medium, preferably a pyrogen-free physiological saline or 5% dextrose in water, as used for parenteral fluid replacement. Reconstitution causes the spontaneous formation of liposomes, which may be refined in size by methods detailed below.

Alternatively, where the liposomes are prepared to contain encapsulated compound, a liposome preparation method which yields high encapsulation efficiency may be preferred. For example, the reverse-phase evaporation method described by Szoka et al., 1980, yields encapsulation efficiencies as high as about 50%. As a result, losses of the encapsulated compound (e.g., a peptide hormone) are minimized. The reverse-phase evaporation vesicles ("REV") produced by this method are predominantly oligolamellar and have heterogeneous sizes which are largely between about 0.3 and 20 microns and average 0.4 to 0.5 microns.

The liposome suspension may be sized to achieve a selective size distribution of vesicles. The sizing serves to eliminate larger liposomes and to produce a defined size range having optimal pharmacokinetic properties.

Several techniques are available for reducing the size and size heterogeneity of liposomes. Sonicating a liposome suspension either by bath or probe sonication produces a progressive size reduction down to small unilamellar vesicles less than about 0.025 microns in size. Homogenization is another method which relies on shearing energy to fragment large liposomes into smaller ones. In a typical homogenization procedure, MLVs are recirculated through a standard emulsion homogenizer or extruded at high shear forces through a small orifice until selected liposome sizes are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution, depending on the pore size of the membrane. Typically, the suspension is cycled through the membrane several times until the desired liposome size distribution is achieved. The liposomes may be extruded through successively smaller-pore membranes, to achieve a gradual reduction in liposome size.

Centrifugation and molecular sieve chromatography are other methods which are available for producing a liposome suspension with reduced particle sizes. These two methods both involve preferential removal of larger liposomes, rather than conversion of large particles to smaller ones. Liposome yields are correspondingly reduced.

Compositions containing the desired compound in liposome can be administered by any of the conventional dosing methods, including oral, subcutaneous, intramuscular, or intravenous administration.

The present invention is further illustrated by the following examples.

EXAMPLES

Example 1—Methods

Animals. Male Sprague-Dawley rats (200–300 grams) or male Swiss-Webster albino mice (20–35 grams) (Taconic Farms, Inc., Germantown, N.Y.) were maintained on a reverse 12-hr light/dark cycle (lights on 19:00, light off 07:00) and used for nociceptive testing. All experiments were reviewed and approved by the Institutional Animal Care and Use Committee of Albany Medical College.

Drugs and solutions. Cimetidine and SKF92374 were dissolved in HCl (1.0–1.2N), titrated to a pH between 5.5–6.5 and diluted with saline. HA dihydrochloride was dissolved in saline or buffer. In vivo vehicle groups received either saline or sodium maleate in saline. The doses of all drugs shown are those of the base, except for HA and ranitidine, doses of which are given as the dihydrochloride and hydrochloride salts, respectively.

Surgery for microinjections. The microinjection apparatus, consisting of a chronically-implanted guide cannula along with a stylet and an injection cannula, has been previously described in detail (Crane and Glick, 1979). Rats were anesthetized with methohexital (50 mg/kg) and supplemented with methoxyflurane. Unilateral guide cannulas were stereotaxically implanted into the brain and anchored to the skull with 3 stainless steel screws and dental cement. After surgery, animals were individually housed with freely available food and water for one week before testing. Guide cannulas were implanted such that injections were made into either the ventral, lateral aspect of the periaqueductal grey at the level of the dorsal raphe ("PAG/DR") or the left lateral ventricle. Coordinates (in mm from bregma (Paxinos and Watson, 1988) for the guide cannulas were PAG/DR: AP−7.8, ML+1.8, DV−3.8, 14° angle from vertical (see Thoburn et al., 1994 and Hough and Nalwalk, 1992, for illustrations of PAG/DR injection sites); lateral ventricle (intraventricular): AP−0.8, ML+1.5, DV−3.3, 0° angle. Injection cannulas were made to extend ventrally 1 and 2 mm beyond the tip of the guides for intraventricular and PAG/DR injections, respectively. Each animal was only used for a single experiment.

Microinjections and nociceptive testing (rats). Two nociceptive tests were used: the radiant heat tail flick test (D'Amour and Smith, 1941) and the hot plate test (Eddy and Leimbach, 1953). For the tail flick test, the radiant heat source was set such that baseline latencies were generally between 3 and 4 s, with a 15 s cutoff. The heat source was not adjusted for individual animals. The ventral surface of tail (2–5 cm from the tip) was exposed to radiant heat and the latency for tail movement was recorded. For the hot plate test, animals were placed on a 52° surface, and the latency to a hind paw lift or lick was recorded, with a maximal exposure of 60 s. Baseline latencies were 9 to 12 seconds. Three to seven hours into the dark portion of the diurnal cycle, animals were tested for baseline nociception (one hot plate test followed by three tail flick tests). Animals were gently secured by wrapping with a laboratory pad, the stylet was removed, and the injection cannula was inserted. Drugs were injected manually (a total volume of 0.5 μl over 1 min in the PAG/DR experiments or 5 μl over 5 min in the intraventricular experiments). Successful injection was assured by following movement of an air bubble in the tubing between the syringe and the cannula and by the absence of leakage. One minute after the end of the infusion, the injection cannula was removed and the stylet replaced. Animals were re-tested with single hot plate and tail flick tests at 5, 10, and 30 min after the replacement of the stylet. Each tail flick test was performed 1 min after a hot plate test. No tail flick tests were performed in the PAG/DR intracerebral study. At the end of each experiment, animals received intraperitoneal pentobarbital (50 mg/kg) and intracerebral (0.5 μl) or intraventricular (5 μl) injections of India Ink. Following intracerebral injections, the brain was removed, frozen, sectioned at 20 μm, and stained with Susan Black and Neutral Red (Shapiro et al., 1983) to verify the injection sites. Data from animals whose placements were outside the target area or who had unsuccessful injections were excluded. Successful intraventricular injections were verified by observing the proper distribution of ink throughout the ventricular system.

Microinjections and nociceptive testing (mice). Mice were tested by the tail-immersion nociceptive test (Sewell and Spencer, 1976) with a water temperature of 55°. Control latencies and cutoff latencies were 1–2 and 8 sec, respectively. Following baseline testing, mice were lightly anesthetized with ether, and microinjections (2 μl, 1 min infusion) were made into the lateral ventricle by use of a stereotaxically drilled Plexiglass block applied to the skull as previously described (Glick et al., 1975; Hough et al., 1984). The incision was closed with wound clips. This surgical/anesthesia procedure allowed animals to be fully conscious and to appear normal within 5 min after the injection. India ink was used to verify intraventricular injections in all subjects. Animals were re-tested at the times indicated following the end of the infusion. Mouse experiments with SKF92374 were conducted with mice from normal (i.e. not reversed) light-dark cycles.

Analysis of antinociceptive data. Antinociceptive scores of each animal 5 were calculated as percent of maximum possible effect ("% MPE"), where $$\% MPE = \frac{\text{drug latency} - \text{baseline latency}}{\text{cutoff latency} - \text{baseline latency}} \times 100$$

For the tail flick test, the third latency before the drug treatment was used as the baseline score, since the first 2 scores were higher than the subsequent latencies when no drug was given. Results for each treatment group are given as mean % MPE+S.E.M. One-factor (drug), repeated-measure (time) analysis of variance ("ANOVA") was used to analyze % MPE scores, and LSD post-hoc comparisons were used as needed (Statistica, CSS, Inc., Tulsa, Okla.). Data were fitted by use of iterative non-linear regression methods (Statistica) to the following equation:

$$E = E_{max} - \frac{E_{max}}{\left(1 + \frac{D}{ED_{50}}\right)^n}$$

where E is observed analgesic effect (% MPE), $E_{max}$ is the maximum analgesic effect of the drug (% MPE), D is the dose of drug injected (μg), n is the slope function, and $ED_{50}$ is the dose of drug inducing a 50% of maximum effect (μg). $E_{max}$ was set to be 100% for fitting cimetidine and SKF92374 data, and the parameters $ED_{50}$ and n were estimated. For the HA dose-response data, $E_{max}$ was fitted along with other parameters. Statistical differences in $ED_{50}$ or n values between cimetidine and SKF92374 were assessed within the non-linear regression program (Statistica). In some cases, data were also fitted with the programs RS/1 (BBN Software, Cambridge, Mass.).

Example 2—Analgesic Activity Results.

The analgesic activities of burimamide, SKF92374, norburimamide, metiamide, ranitidine, tiotidine, VUF 4684, VUF 4685, VUF 4686, VUF 4687, VUF 4740, and VUF 5261 are summarized in Table 1. Rats or mice were tested for baseline nociception with either the tail flick ("TF"), hot plate ("EIP"), or tail immersion ("TI") test as described in Example 1. They then received the drug indicated (or saline vehicle) by intracerebroventricular administration and were retested 10 min later. Analgesic data are given as % MPE (mean±S.E.M.), calculated as described for the number of subjects given. Baseline nociceptive scores were not different between groups. ANOVA revealed that all drugs in Table 1 induced significant antinociceptive activity.

TABLE 1

| Species | Drug | Dose (ug) | Tail Flick[†] % MPE | | | Hot Plate % MPE | | |
|---|---|---|---|---|---|---|---|---|
| | | | Mean | S.E.M. | n | Mean | S.E.M. | n |
| Rat | Saline | — | 2.85 | 2.66 | 4 | 0.10 | 0.91 | 4 |
| | Burimamide | 30 | 3.05 | 4.39 | 5 | 19.44** | 4.77 | 5 |
| | | 60 | 100.00** | 0.00 | 5 | 100.00** | 0.00 | 5 |
| | | 100 | 100.00** | 0.00 | 3 | 87.22** | 12.78 | 4 |
| | Norburimamide | 30 | 20.11 | 9.41 | 4 | 25.19* | 7.81 | 6 |
| | | 60 | 79.42** | 20.57 | 4 | 71.12** | 18.69 | 6 |
| | | 100 | 100.00** | 0.00 | 4 | 100.00** | 0.00 | 6 |
| | SKF92374 | 3 | 4.47 | 2.98 | 4 | 7.46 | 5.09 | 4 |
| | | 30 | 7.21 | 3.95 | 4 | 13.45 | 7.16 | 4 |
| | | 60 | 37.32 | 18.47 | 8 | 32.96 | 13.59 | 8 |
| | | 100 | 100.00** | 0.00 | 8 | 89.92** | 10.08 | 8 |
| | | 300 | 100.00** | 0.00 | 5 | 85.56** | 14.44 | 5 |
| | Metiamide | 60 | 4.12 | 3.05 | 6 | 19.17 | 12.62 | 6 |
| | | 100 | 72.83** | 14.84 | 9 | 64.84** | 11.51 | 8 |
| | Ranitidine | 10 | 0.40 | 3.10 | 5 | 8.64 | 4.16 | 5 |
| | | 30 | 28.38 | 21.22 | 5 | 37.28 | 16.17 | 5 |
| | | 90 | 100.00** | 0.00 | 5 | 100.00** | 0.00 | 5 |
| | VUF4740 | 15 | 12.53 | 14.48 | 4 | 30.95 | 23.05 | 4 |
| | | 30 | 65.26** | 21.43 | 5 | 68.52** | 19.74 | 5 |
| | VUF4685 | 10 | 3.47 | 2.92 | 5 | 10.54 | 5.32 | 5 |
| | | 30 | 57.23** | 19.28 | 5 | 68.62** | 7.99 | 5 |
| | | 60 | 92.11** | 7.89 | 5 | 100.00* | 0.00 | 5 |
| | VUF4684 | 30 | −1.99 | 1.93 | 5 | 3.62 | 5.86 | 5 |
| | | 60 | 24.68 | 19.04 | 5 | 17.32* | 4.93 | 5 |
| | | 100 | 79.04** | 20.95 | 5 | 77.10* | 14.38 | 5 |
| | VUF4686 | 15 | 2.46 | 3.80 | 3 | 24.02 | 12.85 | 3 |
| | | 30 | 76.41* | 23.59 | 4 | 76.46* | 23.54 | 4 |
| | VUF4687 | 15 | 3.37 | 1.48 | 5 | 6.02 | 4.42 | 3 |
| | | 30 | 48.62** | 23.00 | 6 | 75.68** | 15.59 | 6 |
| | | 60 | 100.00** | 0.00 | 5 | 100.00** | 0.00 | 5 |
| | VUF5261 | 30 | 27.03 | 24.35 | 4 | 8.42 | 4.87 | 4 |
| | | 45 | 79.80* | 20.20 | 4 | 47.51 | 19.55 | 4 |
| | | 60 | 100.00** | 0.00 | 4 | 100.00** | 0.00 | 4 |
| Mouse | Saline | | 19.84 | 1.48 | 6 | | | |
| | SKF92374 | 3 | 28.24 | 18.28 | 5 | | | |
| | | 10 | 51.03 | 20.54 | 5 | | | |
| | | 30 | 100.00** | 100.00** | 5 | | | |
| | Ranitidine | 30 | 66.70* | 19.90 | 4 | | | |
| | Tiotidine | 10 | 72.14** | 17.87 | 6 | | | |

Figure 1:
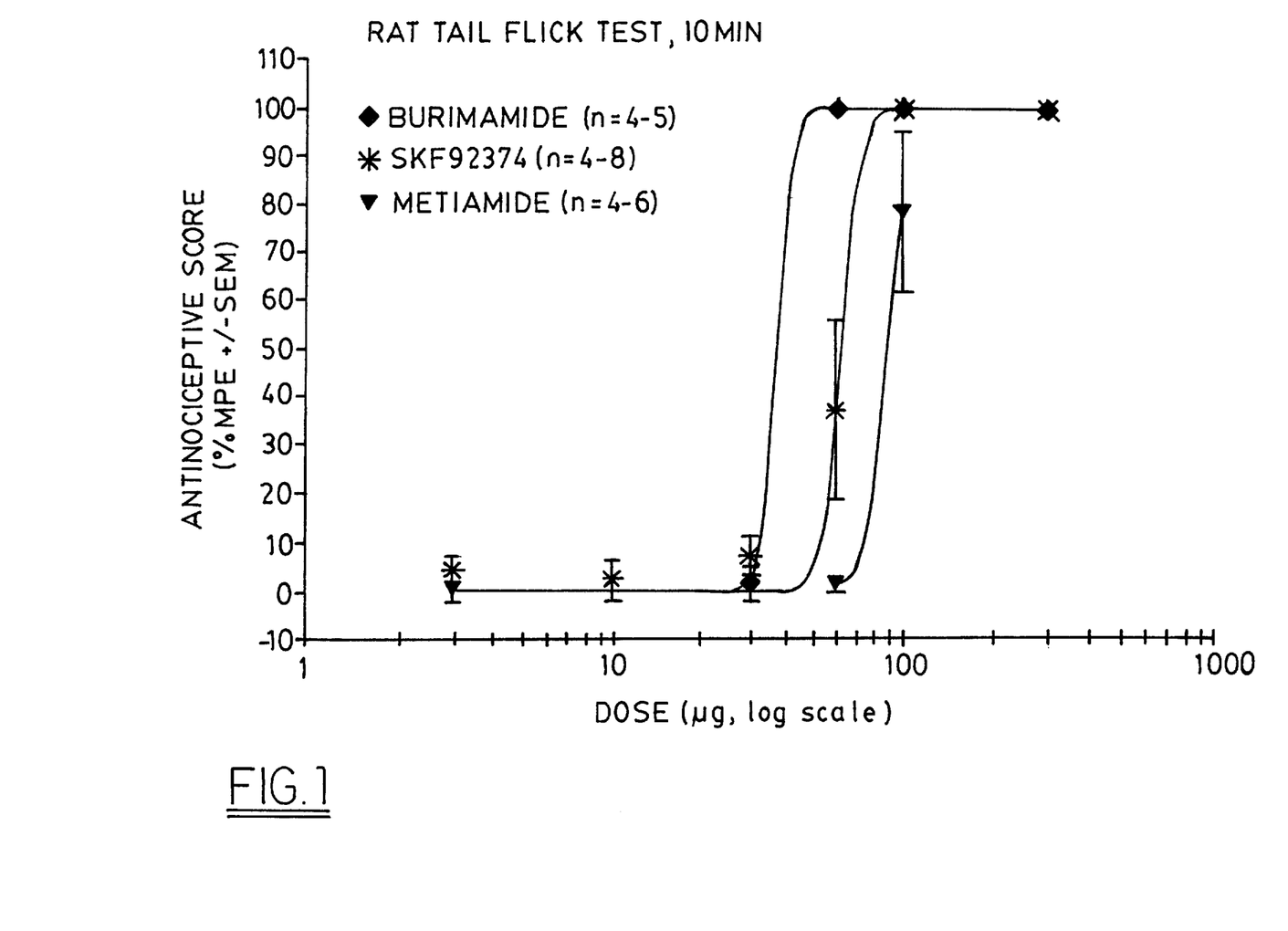
FIG. 1 shows dose-response curves for tail flick analgesic effects of burimamide (diamonds), SKF92374 (stars) and metiamide (inverted triangles) in rats. Rats were tested for baseline responses, received an infusion into the left lateral ventricle (5 µl) and re-tested 10 min later. Doses of drugs (µLg, abscissa, log scale) are plotted against the tail flick antinociceptive scores (mean percent of maximum possible effect ("% MPE")+S.E.M., ordinate) for the number of subjects shown for each drug group. One-factor (drug), repeated-measure (time) analysis of variance ("ANOVA") revealed that all three drugs induced highly significant antinociceptive effects. Baseline scores were not different between the groups.
Figure 2:
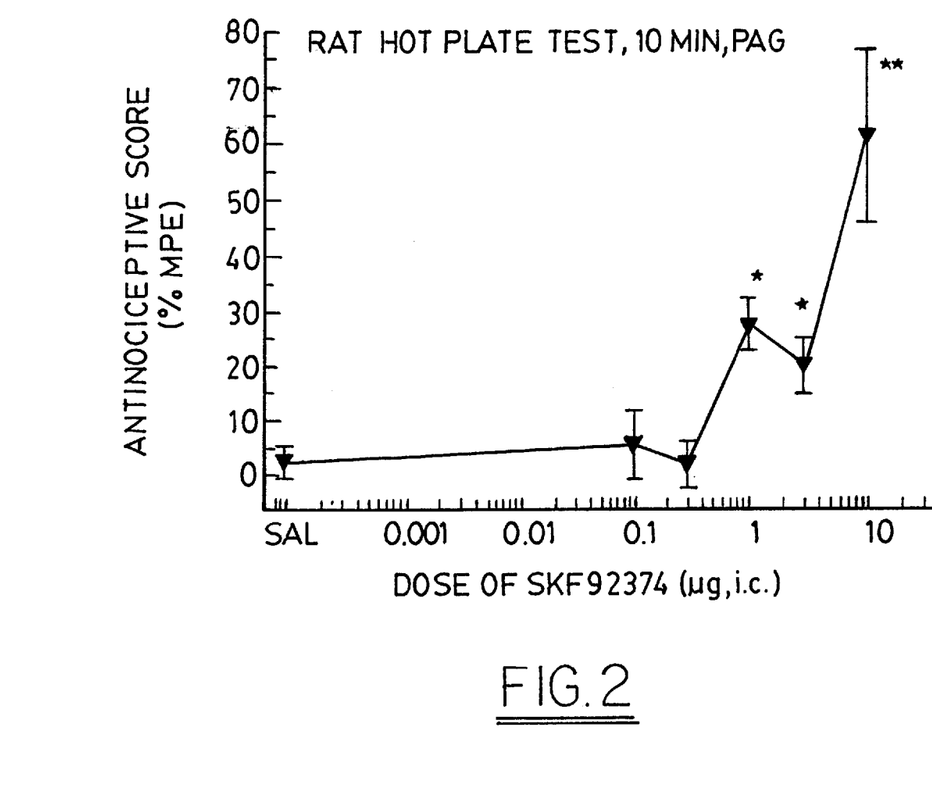

*,**Significantly different from saline treatment in the same species and test (P < 0.02, 0.001, respectively).
[†]Tail Immersion test in mice FIG. 1 demonstrates the analgesic activity of burimamide, SKF92374, and metiamide. All compounds induced dose-related analgesic responses in rats on the tail flick test, and all three compounds also were capable of inducing 100% response levels (i.e. inducing complete analgesic responses). FIG. 2 shows that these compounds are also active after intracerebral administration. SKF92374 induced analgesic responses after intracerebral microinjection into the periaqueductal grey, a midbrain area known to participate in the modulation of pain transmission. As Table 1 shows, norburimamide also induced dose-related analgesic responses similar to those found after burimamide treatment. Furthermore, Table 1 indicates that these compounds are active in the hot plate nociceptive test, and that the furan (ranitidine) and thiazole (tiotidine) also induced analgesia in the mouse tail immersion test.

Example 3—Antinociceptive Effects of Intraventricular-Administered Drugs.

Figure 3A:
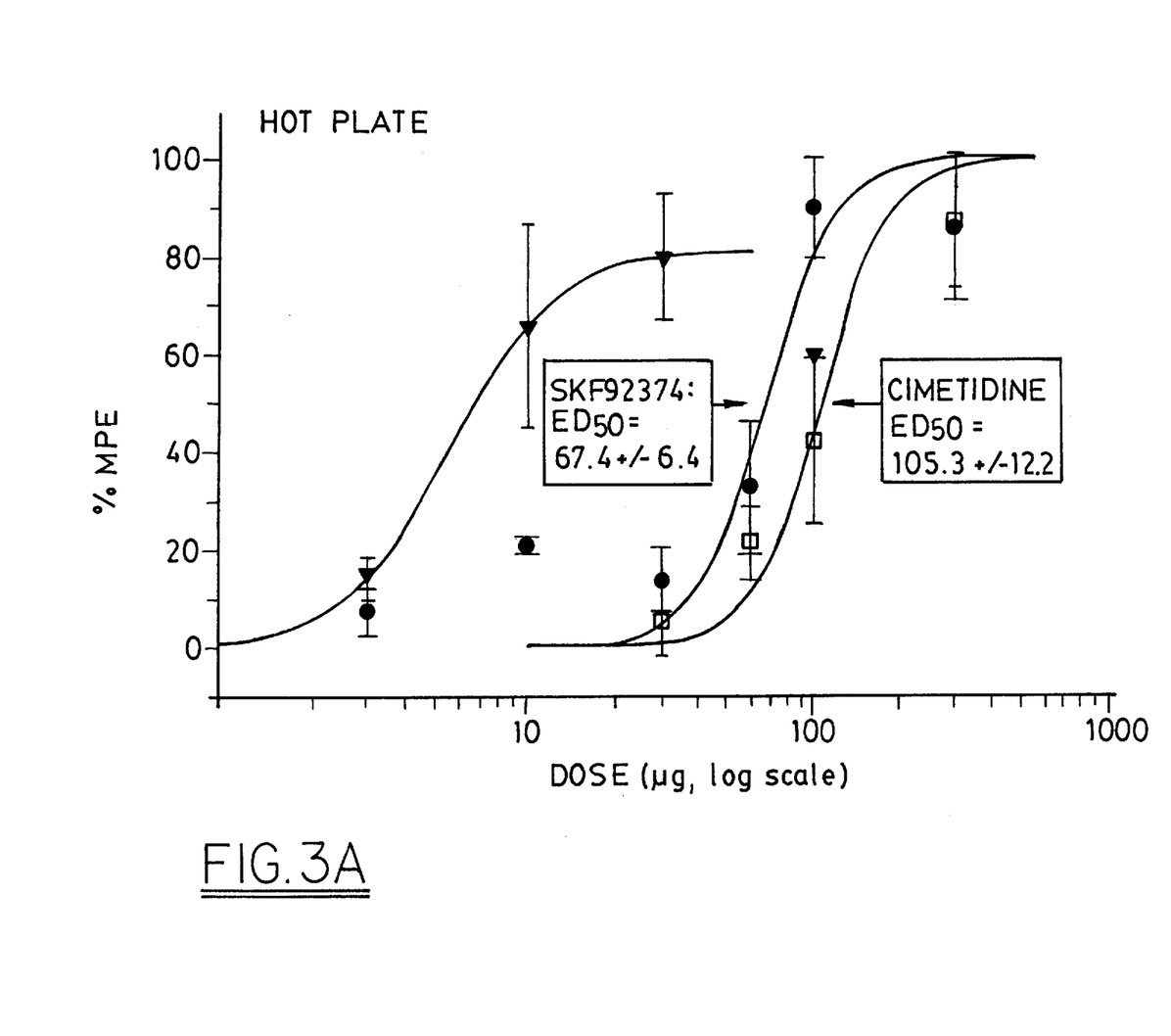
Figure 3B:
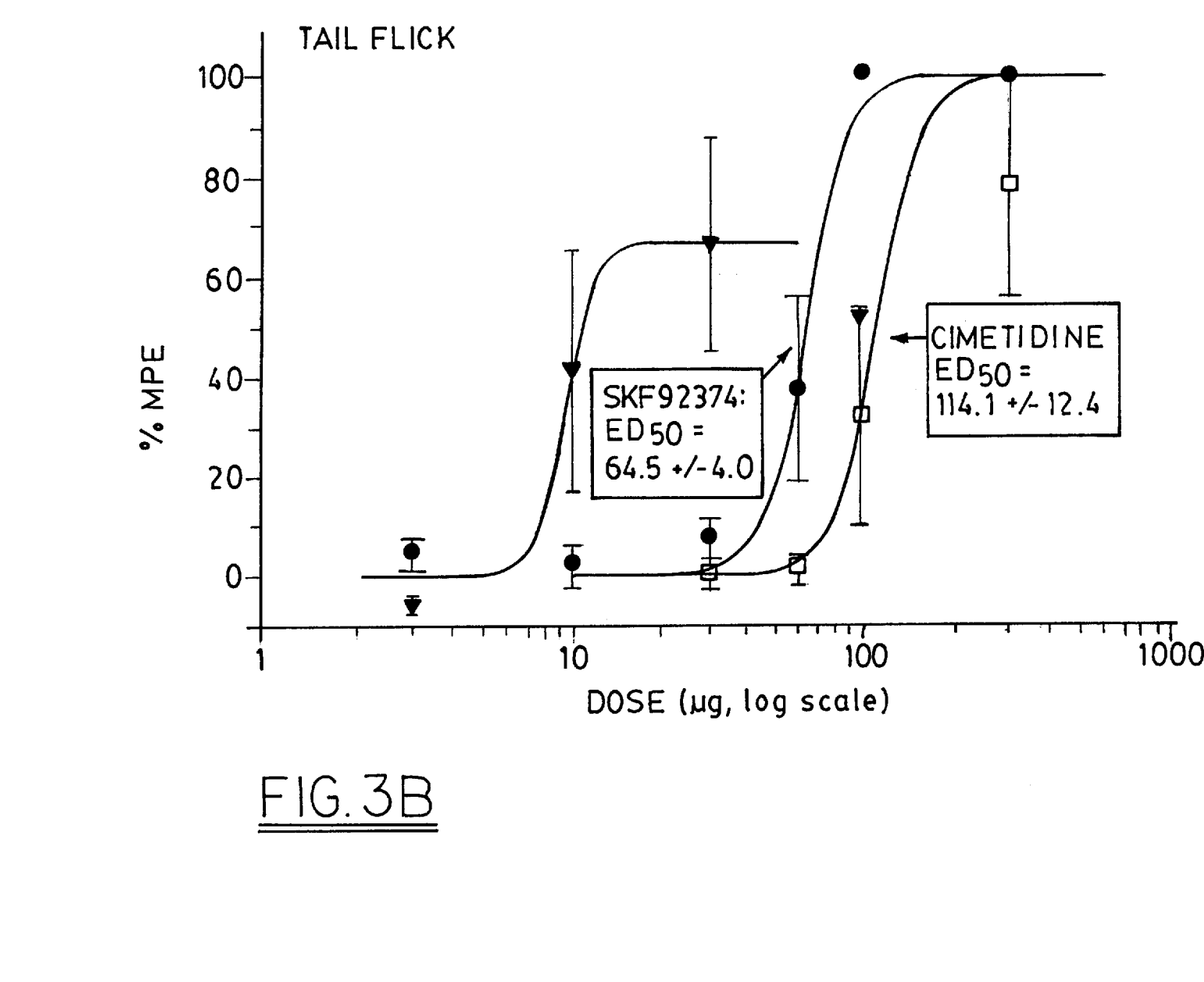

Three compounds (HA, cimetidine, and SKF92374) were tested over a broad dosage range at 3 times on both the hot plate and tail flick tests. ANOVA of these results for each agent indicated significant drug and time effects (P<0.01) for HA, cimetidine, and SKF92374 on both nociceptive tests. Antinociceptive responses were highest at 10 min on the hot plate test and 5–10 min on the tail flick test. Thus, 10 min data points were used to illustrate dose-response results (FIG. 3). As shown, both cimetidine (30–300 μg) and SKF92374 (3–300 μg) induced pronounced, dose-related antinociceptive effects (P<0.05) on both nociceptive tests. Statistical comparison of the dose-response curves of cimetidine and SKF92374 indicated no significant differences (P>0.05) in slopes on either nociceptive test. When these data were fitted to common slopes (n=3.7 and 5.9 for hot plate and tail flick tests, respectively), $ED_{50}$ values were estimated for these compounds (cimetidine: 105.3±12.2, 114.1±12.4 μg; SKF92374; 67.4±6.4, 64.5±4.0 μg for hot plate and tail flick tests, respectively). Statistical comparisons of estimated $ED_{50}$ values for cimetidine and SKF92374 found the latter to be significantly more potent than the former on both nociceptive tests (P<0.02). HA also induced significant antinociception at 10–100 μg. However, the largest dose (100 μg) did not cause the maximal effect, resulting in an inverted U-shaped dose-response curve (FIGS. 3A and 3B). Fitting of the dose-related portion of these results (3–30 μg) yielded estimates of $ED_{50}$ (5.5, 9.4 μg), slope function (n=2.5, 8.3), and $E_{max}$ (81.3%, 66.5%) for HA on the hot plate and tail flick tests, respectively.

Although the invention has been described in detail for the purpose of illustration, it is understood that such detail is solely for that purpose, and variations can be made therein by those skilled in the art without departing from the spirit and scope of the invention which is defined by the following claims.

LIST OF REFERENCES CITED

Allen and Everest, "Effect of liposome size and drug release properties on pharmacokinetics of encapsulated drug in rats," *J. Pharmacol. Exp. Ther.,* 226:539–544 (1983).

Arrang et al., "4-Imidazolyl)piperidines, the Preparation Thereof and Their Application in Therapy," U.S. Pat. No. 4,707,487, Nov. 17, 1987.

Bhattacharya and Parrnar, "Antinociceptive effect of intracerebroventicularly administered histamine in rats," *Res. Comm. Chem. Path. Pharmacol.,* 49:125–136 (1985).

Braga et al., "Electrophysiological correlates for antinociceptive effects of histamine after intracerebral administration to the rat," *Neuropharmacology,* 31:937–941 (1992).

Chung et al., "Analgesic effect of histamine induced by intracerebral injection into mice," *Agents Actions,* 15:137–142 (1984).

Crane and Glick, "Simple cannula for repeated intracerebral drug administration in rats," *Pharmacol. Biochem. Behav.,* 10:799:800 (1979).

D'Amour and Smith, "A method for determining loss of pain sensation," *J. Pharmacol. Exp. Ther.,* 72:74–79 (1941).

Deamer and Uster, "Liposome preparations: methods and mechanisms," in M. Ostro, ed., *Liposomes,* New York-:Marcel Dekker, Inc., pp. 27–51 (1983).

Durant et al, "N-Cyano-N'-heterocyclic-alkyl quanidine inhibitors of $H_2$ histamine receptors," U.S. Pat. No. 3,975,530, Aug. 17, 1976.

Durant et al., "Cyanoguanidinie-thiourea equivalence in the development of the histamine $H_2$ receptor antagonist, cimetidine," *J. Med. Chem.,* 20: 901–906 (1977).

Eddy and Leimbach, "Synthetic analgesics, II Dithienylbutenyl and dithienylbutylamines," *J. Pharmacol. Exp. Ther.,* 107:385–393 (1953).

Fresta et al., "Liposomes as in-vivo carriers for citicoline: effects on rat cerebral post-ischaemic reperfusion," *J. Pharm. Pharmacol,* 46:974–981 (1994).

Glick and Crane, "Opiate-like and abstinence-like effects of intracerebral histamine administration in rats," *Nature,* 273:547–549 (1978).

Glick et al., "Effects of N-Hydroxyethly-pyrrolidinium methiodide, a choline analogue, on passive avoidance behaviour in mice," *Neuropharmacol.,* 14:561–564 (1975).

Gogas and Hough, "Inhibition of naloxone—resistant analgesia by centrally-administered $H_2$ antagonists," *J. Pharmacol. Exp. Ther.,* 248:262–267 (1989).

Gogas et al., "Opposing actions of cimetidine on naloxone-sensitive and naloxone-insenstitive forms of footshock-induced analgesia," *Brain Res.,* 370:370–374 (1986).

Hough and Nalwalk, "Modulation of morphine antinociception by antagonism of $H_2$ receptors in the periaqueductal gray," *Brain Res.,* 588:58–66 (1992).

Hough et al., "No evidence for histamine-mediated morphine analgesia," *Neuropharmacol.,* 23:705–709 (1984).

Jones and Yellin, "Guanidino imidazoles and thiazoles," U.S. Pat. No. 4,165,377, Aug. 21, 1979.

Leza et al., "$H_1$- and $H_2$-histamine receptor blockers and opiate analgesia in mice," *Methods Find. Exp. Clin. Pharm.,* 12:671–678 (1990).

Madrid et al., "New directions in the delivery of drugs and other substances to the central nervous system," *Adv. Pharmacol.,* 22:299–323 (1991).

Malmberg-Aiello et al., "Role of histamine in rodent antinociception," *Br. J. Pharmacol.,* 111:1269–1279 (1994).

Netti et al., "Antinociceptive effect of centrally administered cimetidine and dimaprit in the rat," *Pharmacology,* 28:262–267 (1984).

Netti et al., "Central effects of histamine $H_2$-receptor agonists and antagonists on nociception in the rat," *Agents Actions,* 23:247–249 (1988).

Netti et al., "Evidence for an inhibitory role of central histamine on carrageenin-induced hyperalgesia," *Neuropharmacology,* 33:205–210 (1994).

Neuwelt, et al., "Osmotic blood-brain barrier modification and combination chemotherapy: concurrent tumor regression in areas of barrier opening and progression in brain regions distant to barrier opening," *Neurosurgery,* 15:362–366 (1984).

Oluyomi and Hart, "Involvement of histamine in naloxone-resistant and naloxone-sensitive models of swin stress-induced antinociception in the mouse," *Neuropharmacology,* 30:1021–1027 (1991).

Onodera and Ogura, "Opiate-like actions by intracerebronventricular histamine in mice and its antagonism by naloxone," *Jap. J. Oral Biol.,* 25:1144–1147 (1983).

Pardridge, "Recent developments in peptide drug delivery to the brain," *Pharmacol. & Toxicol.,* 71:3–10 (1992).

Parolaro et al., "Histamine as a central modulator of rat intestinal transit," *J. Pharmacol. Exp. Ther.,* 249:324–328 (1989).

Paxinos and Watson, *The Rat Brain in Stereotaxic Coordinates,* Sydney:Academic Press (1988).

Price et al., "Aminoalkyl furan derivatives," U.S. Pat. No. 4,128,658, Dec. 5, 1978.

Robertson et al., "Potentiation of opioid and nonopioid forms of swin analgesia by cimetidine," *Pharmacol. Biochem. Behav.,* 31:107–112 (1988).

Schwartz et al., "A Thrid Histamine Receptor Subtype: Characterisation, Localisation and Functions of the $H_3$ Receptor," *Agents Actions,* 30:13–23 (1990).

Sewell and Spencer, "Antinociceptive activity of narcotic agonist and partial agonist analgesics and other agents in the tail-immersion test in mice and rats," *Neuropharmacol.,* 15:683–688 (1976).

Shapiro et al., "A simple and rapid technique for preparing histological sections of brain," *Pharmacol. Biochem. Behav.,* 19:1049–1050 (1983).

Sibilia et al., "Central antinociceptive action of histamine: Behavioural and electrophysiological studies," *Agents Actions,* 35 Suppl. C:C350–C353 (1992).

Szoka et al., *Am. Rev. Biophys. Bioeng.,* 9:467 (1980).

Thoburn et al., "Histamine-induced modulation of nociceptive responses," *Pain,* 58:29–37 (1994).

Tsuzuki et al., "Adamantane an a brain-directed drug carrier for poorly absorbed drug: antinociceptive effects of [D-Ala$^2$]Leu-enkephalin derivatives conjugated with the 1-adamantane moiety," Biochem. Pharmacol., 41:R5–R8 (1991).

Vollinga et al., "H. A. simple and rapid in vitro test system for the screening of histamine $H_3$ ligands," *Methods Find. Exp. Clin. Pharmacol.,* 14:747–751 (1992).

Vollinga et al., "New Analogs of Burimamide as Potent and Selective Histamine $H_3$ Receptor Antagonists: The Effect of Chain Length Variation of the Alkyl Spacer and Modifications of the N-thiourea Substituent," *J. Med. Chem.,* 38:2244–2250 (1995).

What is claimed:

1. A method for inhibiting pain in a subject comprising: providing a compound having the formula:

wherein
  Z represents the atoms necessary to complete a five-membered or six-membered heterocyclic ring;
  D is a 1-piperid-4-yl moiety, a —Q—NH— moiety, or a —Q—S— moiety;
  Q has the formula —$(CH_2)_m$—$(Y)_s$—$(CH_2)_n$—, wherein Y is O, S, Se or NH, m is an integer from 0 to 5, n is an integer from 0 to 5, and s is 0 or 1;
  $R^1$ is H, $R^3$ or $R^4$;
  $R^2$ is $R^3$;
  each of $A^1$ and $A^2$ is H or $A^1$ and $A^2$ taken together form a second bond between the carbon atoms bearing $A^1$ and $A^2$;
  X is S, N—CN, $CHNO_2$, O, or NH, provided that when D is a —Q—S— moiety, X is NH;
  $R^3$ is selected from the group consisting of substituted or unsubstituted alkyls; substituted or unsubstituted 4-8-membered homocyclic rings; substituted or unsubstituted 4-8-membered heterocyclic rings; substituted or unsubstituted fused multicyclic rings;
  $R^4$ is a moiety having the formula:

—W—T

—W— is —O—, —S—, —S—S—, —C(O)—O—, —C(O)—S—, —C(O)—N($R^5$)—, —N($R^5$)—, or CH=N—;
  T is selected from the group consisting of substituted or unsubstituted alkyls, substituted or unsubstituted 4-8-membered homocyclic rings, substituted or unsubstituted 4-8-membered heterocyclic rings, substituted or unsubstituted fused multicyclic rings, and proteinaceous transport vectors; and
  $R^5$ is H, substituted alkyl, or an unsubstituted alkyl,
  provided that when $A^1$ and $A^2$ taken together form a second bond between the carbon atoms bearing $A^1$ and $A^2$, X is N—CN or S, and Z is —NH—CH=N—, Q is not —$CH_2SCH_2CH_2$—
or a pharmaceutically acceptable salt thereof; and
administering to said subject an amount of the compound effective to inhibit pain.

2. A method according to claim 1, wherein the five-membered or six-membered ring is substituted.

3. A method according to claim 1, wherein $A^1$ and $A^2$ taken together form a second bond between the carbon atoms bearing $A^1$ and $A^2$, Y is S, m is 1, n is an integer from 2 to 5, and s is 0 or 1.

4. A method according to claim 3, wherein Z is —NH—CH=N—.

5. A method according to claim 4, wherein s is 0.

6. A method according to claim 5, wherein n is 3.

7. A method according to claim 6, wherein X is S.

8. A method according to claim 7, wherein $R^1$ is H and $R^2$ is $CH_3$.

9. A method according to claim 7, wherein $R^1$ is H and $R^2$ is phenyl.

10. A method according to claim 7, wherein $R^1$ is H and $R^2$ is benzyl.

11. A method according to claim 7, wherein $R^1$ is H and $R^2$ is phenylethyl.

12. A method according to claim 7, wherein $R^1$ is H and $R^2$ is cyclohexyl.

13. A method according to claim 5, wherein n is 2.

14. A method according to claim 9, wherein X is N—CN.

15. A method according to claim 14, wherein $R^1$ is H and $R^2$ is $CH_3$.

16. A method according to claim 13, wherein X is S.

17. A method according to claim 16, wherein $R^1$ is H and $R^2$ is $CH_3$.

18. A method according to claim 5, wherein n is 5.

19. A method according to claim 18, wherein X is S.

20. A method according to claim 19, wherein $R^1$ is H and $R^2$ is $CH_3$.

21. A method according to claim 19, wherein $R^1$ is H and $R^2$ is phenyl.

22. A method according to claim 4, wherein s is 1.

23. A method according to claim 22, wherein n is 2.

24. A method according to claim 23, wherein X is S.

25. A method according to claim 24, wherein $R^1$ and $R^2$ are each $CH_3$.

26. A method according to claim 3, wherein Z is —S—$CR^6$=N— and $R^6$ is H, a substituted alkyl, an unsubstituted alkyl, a substituted amine, an unsubstituted amine, a substituted imine, or an unsubstituted imine.

27. A method according to claim 26, wherein s is 1 and n is 2.

28. A method according to claim 27, wherein X is N—CN.

29. A method according to claim 28 wherein $R^1$ is H, $R^2$ is $CH_3$, and $R^6$ is N=C$(NH_2)_2$.

30. A method according to claim 3, wherein Z is —CH=$CR^6$—O— and $R^6$ is H, a substituted alkyl, an unsubstituted alkyl, a substituted amine, an unsubstituted amine, a substituted imine, or an unsubstituted imine.

31. A method according to claim 30, wherein s is 1 and n is 2.

32. A method according to claim 31, wherein X is $CHNO_2$.

33. A method according to claim 32, wherein $R^1$ is H, $R^2$ is $CH_3$, and $R^6$ is $CH_2N(CH_3)_2$.

34. A method according to claim 1, wherein D is a 1-piperid-4-yl moiety.

35. A method according to claim 34, wherein $A^1$ and $A^2$ taken together form a second bond between the carbon atoms bearing $A^1$ and $A^2$ and Z is —NH—CH=N—.

36. A method according to claim 35, wherein X is S.

37. A method according to claim 36, wherein $R^1$ is H and $R^2$ is $CH_3$.

38. A method according to claim 36, wherein $R^1$ is H and $R^2$ is phenyl.

39. A method according to claim 1, wherein the compound is brain penetrating.

40. A method according to claim 39, wherein at least one of $R^1$ and $R^2$ is lipophilic.

41. A method according to claim 1, wherein said administering the compound comprises administering the compound orally.

42. A method according to claim 41, wherein the amount is from about 3 to about 25 mg/kg of the subject's body weight.

43. A method according to claim 1, wherein said administering the compound comprises administering the compound parenterally.

44. A method according to claim 43, wherein the amount is from about 1 to about 8 mg/kg of the subject's body weight.

45. A method according to claim 1, wherein said administering the compound comprises injecting the compound intraventicularly.

46. A method according to claim 45, wherein the amount is from about 5 to about 40 mg.

47. A method according to claim 1, wherein said administering the compound comprises injecting the compound intracerebrally.

48. A method according to claim 47, wherein the amount is from about 30 to about 100 μg.

49. Method according to claim 1, wherein the compound is administered in a formulation containing the compound and a sustained release matrix and wherein said administering comprises implanting the formulation into the subject's brain.

50. A method according to claim 1, further comprising:
administering to the subject a material which enhances brain penetration of the compound.

51. A method according to claim 50 a wherein the material is co-administered in a formulation comprising the material and the compound.

52. A method according to claim 51, wherein the material is a liposome and wherein the formulation comprises the compound encapsulated in the liposome.

53. A method according to claim 50, wherein the material is administered separately from the compound.

54. A method according to claim 53, wherein the material is a hyperosmotic sugar solution.

55. A method for inhibiting pain in a subject comprising:
providing a compound having the formula:

wherein
Z represents the atoms necessary to complete a five-membered or six-membered heterocyclic ring;
D is a 1-piperid-4-yl moiety, a —Q—NH— moiety, or a —Q—S— moiety;
Q has the formula —(CH$_2$O$_m$)—(Y)$_s$—(CH$_2$O$_n$)—, wherein Y is O, S, Se or NH, m is an integer from 0 to 5, n is an integer from 0 to 5, and s is 0 or 1;

$R^1$ is H, $R^3$ or $R^4$;

$R^2$ is $R^3$;

each of $A^1$ and $A^2$ is H or $A^1$ and $A^2$ taken together form a second bond between the carbon atoms bearing $A^1$ and $A^2$;

X is S, N—CN, CHNO$_2$, O or NH, provided that when D is a —Q—S— moiety, X is NH;

$R^3$ is selected from the group consisting of substituted or unsubstituted alkyls; substituted or unsubstituted 4-8-membered homocyclic rings; substituted or unsubstituted 4-8-membered heterocyclic rings; substituted or unsubstituted fused multicyclic rings;

$R^4$ is a moiety having the formula:

—W—T

—W— is —O—, —S—, —S—S—, —C (O)—O—, —C (O)—S—, —C(O)—N($R^5$)—, —N($R^5$)—, or CH=N—;

T is selected from the group consisting of substituted or unsubstituted alkyls, substituted or unsubstituted 4-8-membered homocyclic rings, substituted or unsubstituted 4-8-membered heterocyclic rings, substituted or unsubstituted fused multicyclic rings, and proteinaceous transport vectors; and $R^5$ is H, substituted alkyl, or an unsubstituted alkyl, provided that when $A^1$ and $A^2$ taken together form a second bond between the carbon atoms bearing $A^1$ and $A^2$, X is N—ON or S, and Z is —NH—CH=N—, Q is not —CH$_2$SCH$_2$CH$_2$— or a pharmaceutically acceptable salt thereof;

altering the compound to make the compound brain-penetrating; and administering to said subject an amount of the altered compound effective to inhibit pain.

56. A method according to claim 1, wherein the five-membered or six-membered ring is unsubstituted.

* * * * *